(12) United States Patent
Kwon et al.

(10) Patent No.: US 9,328,366 B2
(45) Date of Patent: May 3, 2016

(54) METHOD FOR MASS PRODUCTION OF HIGH-PURITY OLIGONUCLEOTIDES

(75) Inventors: Sunghoon Kwon, Seoul (KR); Hyoki Kim, Seoul (KR); Howon Lee, Seoul (KR); Sungsik Kim, Daejeon (KR); Taehoon Ryu, Seoul (KR)

(73) Assignee: SNU R & DB FOUNDATION, Seoul (KR)

( * ) Notice: Subject to any disclaimer, the term of this patent is extended or adjusted under 35 U.S.C. 154(b) by 0 days.

(21) Appl. No.: 13/524,029

(22) Filed: Jun. 15, 2012

(65) Prior Publication Data

US 2013/0109059 A1    May 2, 2013

(30) Foreign Application Priority Data

Oct. 27, 2011  (KR) .................. 10-2011-0110383

(51) Int. Cl.
| | | |
|---|---|---|
| C12P 19/34 | (2006.01) | |
| B01J 19/00 | (2006.01) | |
| C40B 20/02 | (2006.01) | |
| C40B 50/14 | (2006.01) | |
| C40B 60/04 | (2006.01) | |

(52) U.S. Cl.
CPC ............ *C12P 19/34* (2013.01); *B01J 2219/005* (2013.01); *B01J 2219/00315* (2013.01); *B01J 2219/00441* (2013.01); *B01J 2219/00468* (2013.01); *B01J 2219/00596* (2013.01); *B01J 2219/00648* (2013.01); *B01J 2219/00691* (2013.01); *B01J 2219/00693* (2013.01); *B01J 2219/00722* (2013.01); *C40B 20/02* (2013.01); *C40B 50/14* (2013.01); *C40B 60/04* (2013.01)

(58) Field of Classification Search
None
See application file for complete search history.

(56) References Cited

U.S. PATENT DOCUMENTS

| | | | |
|---|---|---|---|
| 5,378,508 A | 1/1995 | Castro et al. | |
| 6,469,779 B2 | 10/2002 | Baer et al. | |
| 2004/0023019 A1* | 2/2004 | Vandenberg et al. | ......... 428/323 |
| 2010/0216648 A1 | 8/2010 | Staehler et al. | |

FOREIGN PATENT DOCUMENTS

WO    WO 2006091868 A2 *  8/2006

OTHER PUBLICATIONS

Salomon, "A massively parallel approach to deformable matching of 3D medical images via stochastic differential equations," Parallel Computing, vol. 31, pp. 45-71, 2005.*
Christensen, "Deformable templates using large deformation kinematics," Image Processing, IEEE Transactions on, vol. 5 p. 1435-1447, 1996.*
Jingdong Tian et al., Accurate multiplex gene synthesis from programmable DNA microchips, Nature, Dec. 2004, pp. 1050-1054, vol. 432.
Jingdong Tian et al., Advancing high-throughput gene synthesis technology, Molecular BioSystems, 2009, pp. 714-722.
Daniel G Gibson et al., Chemical synthesis of the mouse mitochondrial genome, Nature Methods, Nov. 2010, pp. 901-905, vol. 7.
Hwangbeom Kim et al., Hierarchical gene synthesis using DNA microchip oligonucleotides, Journal of Biotechnology, 2011, pp. 319-324.
A. P. Blanchard et al., High-density oligonucleotide arrays, Biosensors & Bioelectronics, 1996, pp. 687-690, vol. 11.
Mark Matzas e, High-fidelity gene synthesis by retrieval of sequence-verified DNA identified using high-throughput pyrosequencing, nature biotechnology, Dec. 2010, pp. 1291-1295.
Nathan R Schiele et al., Laser-based direct-write techniques for cell printing, Biofabrication, 2010, IOP Publishing Ltd.
Virginia Espina et al., Laser-capture microdissection, Nature Protocols, 2006, pp. 586-603, vol. 1, Nature Publishing Group.
Craig B. Arnold et al., Laser direct-write techniques for printing of complex materials, MRS Bulletin, Jan. 2007, pp. 23-31, vol. 32.
Stephen P.A. Fodor et al., Light-directed spatially addressable parallel chemical synthesis, Research Article, Feb. 15, 1991, pp. 767-773.
Ji-Yen Cheng et al., Microfluidic ARray Synthesizer (MArS) for rapid preparation and hybridization of custom DNA microarray, Biotechnology and Bioe . . . , Oct. 1, 2009, pp. 400-407.
Xiaochuan Zhou et al., Microfluidic PicoArray synthesis of oligodeoxynucleotides and simultaneous assembling of multiple DNA sequences, Nucleic Acids Rese . . . , 2004, pp. 5409-5417.
Yilmaz Niyaz et al., Non-contact laser microdissection and pressure catapulting: Automation via object-oriented image processing, Medical Laser Application, 2005, pp. 223-232.
A. Ashkin et al., Optical Levitation by Radiation Pressure, Applied Physics Letters, Oct. 15, 1971, pp. 283-285, vol. 19.
Jiayuan Quan et al., Parallel on-chip gene synthesis and application to optimization of protein expression, nature biotechnology, May 2011, pp. 449-453, vol. 29.
P. Serra et al., Preparation of functional DNA microarrays through laser-induced forward transfer, AIP, Aug. 30, 2004, pp. 1639-1641.
Sriram Kosuri et al., Scalable gene synthesis by selective amplification of DNA pools from high-fidelity microchips, nature biotechnology, Dec. 2010, vol. 28.

* cited by examiner

*Primary Examiner* — Eric S Dejong
*Assistant Examiner* — G. Steven Vanni
(74) *Attorney, Agent, or Firm* — Revolution IP, PLLC

(57) ABSTRACT

Provided is a method of mass-producing high-purity nucleotides including providing a sequencing substrate having a clonal library of oligonucleotides on a solid support, sequencing the clonal library, obtaining measured location data of the solid support on the sequencing substrate, mapping pixel data of a signal generated from the solid support given as a result of the sequencing with the measured location data, extracting the solid support having a desired base sequence from the sequencing substrate using the mapping result, and amplifying an oligonucleotide on the extracted solid support to replicate on a large scale.

11 Claims, 10 Drawing Sheets

GENERATION OF SUBDOMAIN $A_{ij}$, $B_{ij}$

FIG. 10

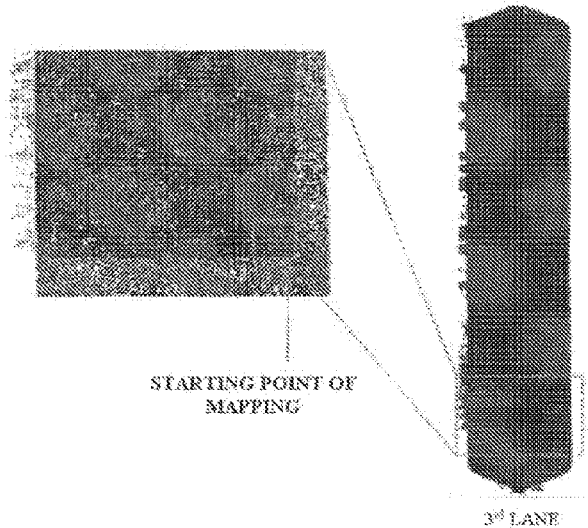

STARTING POINT OF MAPPING

3rd LANE

Matching Results Between Physical Location of Recognized Well and CCD Image Pixels of Each Sequenced Molecular Clone

FIG. 11

| OLIGO ID | BEAD ID | PIXEL X | PIXEL Y | BEAD X | BEAD Y |
|---|---|---|---|---|---|
| 1. OLIGO_NC_011671200KBSELECTION_140 | HGJXWP03GDCR4 | 2495.0 | 946.0 | 7345.3179 | 8139.4494 |
| 2. OLIGO_NC_011671200KBSELECTION_295 | HGJXWP03GAV1M | 2467.5 | 1064.0 | 7875.974 | 10413.3185 |
| 3. OLIGO_NC_011671200KBSELECTION_599 | HGJXWP03HAC2A | 2871.0 | 1298.0 | 48.0154 | 14843.2907 |
| 4. OLIGO_NC_011671200KBSELECTION_627 | HGJXWP03HAPA2 | 2875.5 | 780.0 | 22.74 | 4823.0807 |
| 5. OLIGO_NC_011671200KBSELECTION_714 | HGJXWP03GO32O | 2629.5 | 1102.0 | 4751.1222 | 11131.9501 |
| 6. OLIGO_NC_011671200KBSELECTION_767 | HGJXWP03FMK9L | 2190.5 | 1943.5 | 13102.6089 | 27270.8352 |
| 7. OLIGO_NC_011671200KBSELECTION_799 | HGJXWP03GK0V9 | 2582.0 | 2307.5 | 5336.0856 | 45665.8189 |
| 8. OLIGO_NC_011671200KBSELECTION_895 | HGJXWP03PNJV0 | 2201.0 | 1758.0 | 12944.249 | 23731.0916 |
| 9. OLIGO_NC_011671200KBSELECTION_1058 | HGJXWP03PQQM | 2454.0 | 780.5 | 8155.8318 | 4857.3081 |

METHOD FOR MASS PRODUCTION OF HIGH-PURITY OLIGONUCLEOTIDES

CROSS-REFERENCE TO RELATED APPLICATION

This application claims priority to and the benefit of Korean Patent Application No. 10-2011-0110383, filed Oct. 27, 2011, the disclosure of which is incorporated herein by reference in its entirety.

SEQUENCE LISTING

An attached Sequence Listing is generated as i. name: SEQCRF_582-0011, ii. date of creation: Oct. 14, 2013, and iii. size: 2 KB in computer readable form (CRF).

BACKGROUND

1. Technical Field

The present disclosure relates to a method of mass-producing high-purity nucleotides at a high speed.

2. Discussion of Related Art

In practice, the major obstacles to developing the field of synthetic biology are high price and low purity of DNA, which is a basic material for research of synthetic biology. Over the past decade, while the price of DNA has stayed at 1 dollar per base, the purity of a DNA sequence synthesized with a relatively long length has drastically fallen such that there are economic, temporal and mathematical limits to assembling bases to have a significant sequence length and applying the DNA sequence. For example, a microarray method for synthesizing DNA using an inkjet or light irradiation technique can synthesize at least several millions of kinds of independent DNA through a single synthesis process, thereby dramatically reducing the price of DNA. However, the purity of the synthesized DNA is lower than that of the conventional chemically synthesized sequence, and it is difficult to physically separate the synthesized DNAs for post-processing based on the kind of DNA sequence, due to the characteristic of an extraction technique. Recently, to solve these problems, Matzas, M., et al. suggested a technique of analyzing millions of DNA synthesized by microarray using a next generation DNA sequencer, picking microbeads having only one kind of DNA by a pick-and-place method, and repairing and amplifying the DNA [Matzas, M., et al. High-Fidelity Gene Synthesis by Retrieval of Sequence-Verified DNA Identified Using High-Throughput Pyrosequencing. *Nat. Biotechnol.* 28, 1291-1294 (2010)]. However, this paper only proves the concept, and therefore it is difficult to apply to genome-level research handling a large quantity of DNA because it takes much time, for example, at least several tens of minutes, to practically pick beads. In addition, this thesis does not suggest a general technique of tracing an exact location of a microbead to extract. Moreover, the pick-and-place method has a basic problem of cross-contamination.

SUMMARY

The present disclosure is directed to providing a method of mass-producing high-purity nucleotides, including: providing a sequencing substrate having a clonal library of oligonucleotides on a solid support; sequencing the clonal library; obtaining measured location data of the solid support on the sequencing substrate; mapping the measured location data with pixel data of a signal generated from the solid support given by sequencing; extracting the solid support having a desired DNA sequence from the sequencing substrate using the mapping result; and amplifying the oligonucleotides on the extracted solid support to replicate on a large scale.

The present disclosure is also directed to providing a solid support extraction system for mass-producing high-purity nucleotides, including: a first stage equipped with a sequencing substrate accommodating a solid support to which an oligonucleotide of a specific DNA sequence is bound; a first imaging device for observing the sequencing substrate to extract the solid support; a second stage equipped with a matching substrate which is disposed opposite to the sequencing substrate; an extracting device for separating the solid support from the sequencing substrate and transferring it to the matching substrate; and a controlling device for placing a specific region of the sequencing substrate matching the extracting device to separate the solid support. Here, the placing operation is executed using a mapping result between measured location data of the solid support obtained from the first imaging device and pixel data of a signal generated from the solid support.

BRIEF DESCRIPTION OF THE DRAWINGS

The above and other objects, features and advantages of the present disclosure will become more apparent to those of ordinary skill in the art by describing in detail exemplary embodiments thereof with reference to the attached drawings, in which:

FIG. 10 illustrates mapping results between two groups of data shown in an entire domain of a sequencing substrate;

FIG. 11 illustrates combinations of pixel data and location data obtained by mapping;

FIG. 12 illustrates electrophoresis results after beads extracted in a bead extraction system using a laser are amplified by polymerase chain reaction (PCR); and FIG. 13 illustrates alignment of a DNA sequence (SEQ ID NO: 1 corresponding to "454 SEQUENCING RESULT") included in a bead extracted by mapping with a target DNA sequence (SEQ ID NO: 2 corresponding to "SEQUENCE OF DESIRED DNA").

DETAILED DESCRIPTION OF EXEMPLARY EMBODIMENTS

Figure 1:
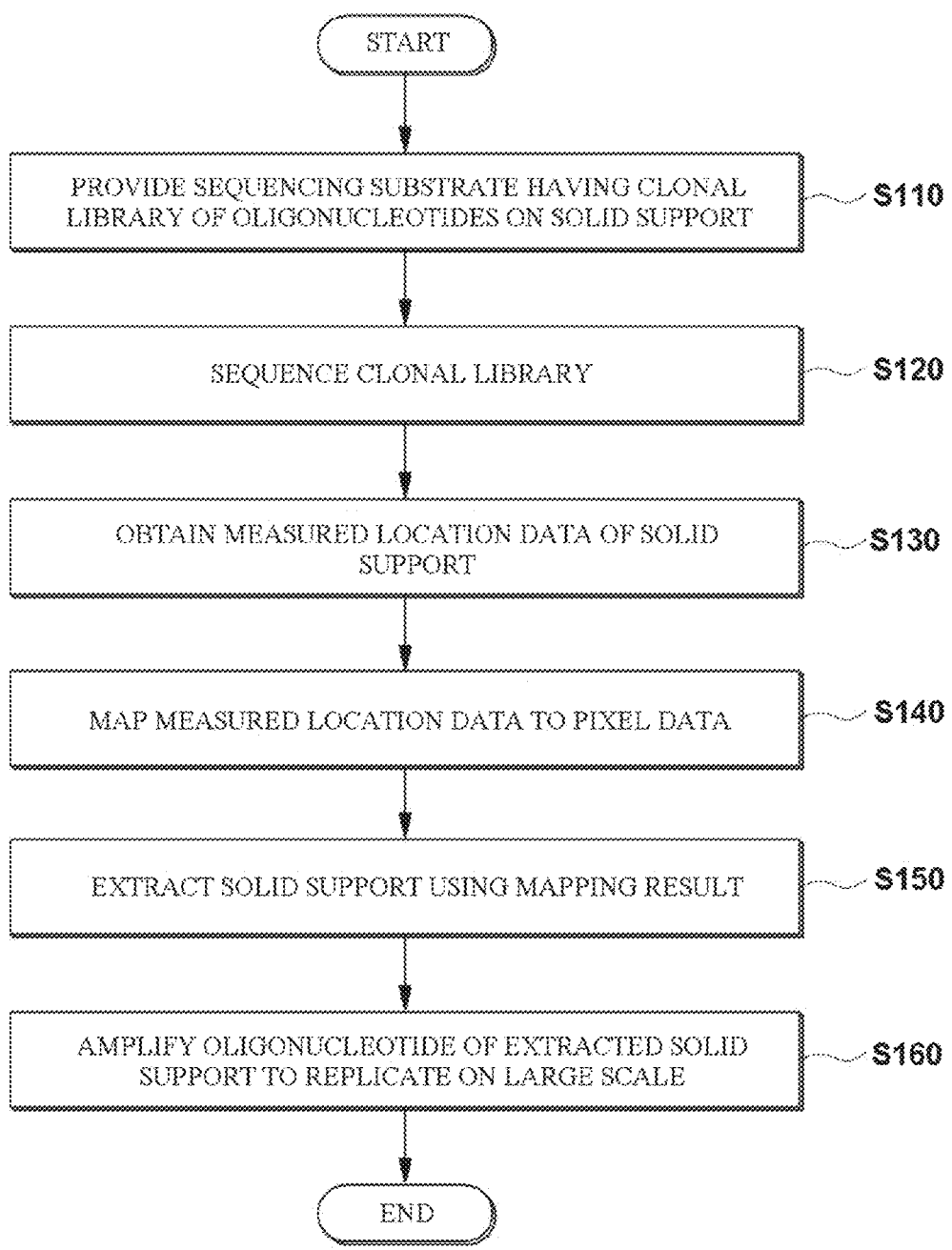
FIG. 1 is a flowchart illustrating a method of mass-producing high-purity nucleotides according to an exemplary embodiment of the present disclosure.

As described in the background, there is a need of a technique for tracing nearest to exact location of a well containing a microbead having a desired specific DNA sequence in an entire domain of a substrate of a next-generation sequencer, and rapidly, precisely and stably extracting the microbead having the desired DNA sequence. A method of mass-producing high-purity nucleotides according to an exemplary embodiment of the present disclosure may rapidly and precisely extract a microbead having a desired specific DNA sequence, and amplify the sequence by an available amount.

Hereinafter, exemplary embodiments of the present disclosure will be described in detail. However, the present disclosure is not limited to the embodiments disclosed below, but can be implemented in various forms. The following embodiments are described in order to enable those of ordinary skill in the art to embody and practice the present disclosure.

It will be understood that, although the terms first, second, A, B, etc. may be used herein in reference to elements of the disclosure, such elements should not be construed as limited by these terms. For example, a first element could be termed a second element, and a second element could be termed a first element, without departing from the scope of the present disclosure. Herein, the term "and/or" includes any and all combinations of one or more referents.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements.

The terminology used herein to describe embodiments of the disclosure is not intended to limit the scope of the disclosure. The articles "a," "an," and "the" are singular in that they have a single referent, however the use of the singular form in the present document should not preclude the presence of more than one referent. In other words, elements of the disclosure referred to in the singular may number one or more, unless the context clearly indicates otherwise. It will be further understood that the terms "comprises," "comprising," "includes," and/or "including," when used herein, specify the presence of stated features, items, steps, operations, elements, and/or components, but do not preclude the presence or addition of one or more other features, items, steps, operations, elements, components, and/or groups thereof.

Exemplary embodiments of the present disclosure will be described in detail below with reference to the appended drawings. Elements of the exemplary embodiments are consistently denoted by the same reference numerals throughout the drawings and detailed description, and elements will only be described once.

FIG. 1 is a flowchart illustrating a method of mass-producing high-purity nucleotides according to an exemplary embodiment of the present disclosure. In S110, a sequencing substrate having a clonal library of oligonucleotides on a solid support is provided. The oligonucleotides may be derived from nature or synthesized. Preferably, oligonucleotides synthesized using a microarray providing at least several millions of kinds of DNA sequences at a low cost are used. Providing the clonal library may include amplifying the oligonucleotide. For amplification, emulsion PCR may be used, and thereby the oligonucleotide is immobilized on a surface of the solid support by a kind of the DNA sequence. The solid supports on which the oligonucleotides are immobilized as described above are disposed in a predetermined section of the sequencing substrate, thereby preparing the clonal library.

The solid support provides a surface to immobilize the oligonucleotides, and may be, but is not limited to, at least one selected from the group consisting of a glass slide, a microbead, a nanoparticle, a nanostructure, a capillary tube, a microfluidic support, a pore structure, a sponge structure, and a dendrimer.

In S120, the clonal library is sequenced. As a result, pixel data of a signal generated from the solid support having a specific DNA may be obtained. The sequencing may be performed by a high-throughput sequencing technique such as a next-generation sequencing (NGS) technique which can highly effectively separate a target DNA with a high purity and show highly analytic efficiency. For example, when the NGS is executed using a microbead as a solid support, the DNA to be analyzed is cut into several hundreds of base pair units, each base pair is attached to an independent microbead and amplified, and then each bead is assembled at a specific location. Through the sequencing, optical or electromagnetic signals sequentially generated according to a kind of DNA sequence may be provided along with location data. The NGS method may simultaneously analyze at least several hundreds of thousands of sequences, thereby having high-throughput, compared with a conventional sequencing method. Accordingly, statistical data for the DNA sequence of a sample to be analyzed may be provided. Since each microbead used herein has one kind of DNA amplified on its surface, when the DNA is extracted and reamplified, a target DNA having a very high purity may be obtained.

In S130, measured location data of the solid support on the sequencing substrate are obtained. To obtain the measured location data, the sequencing substrate may be imaged and an obtained image may be processed. For example, the sequencing substrate may be scanned using an imaging device, and a center of a bead (or well)(that is, the solid support) may be located according to a pattern recognition algorithm. The measured location data is necessary to precisely extract the solid support to which an oligonucleotide having the desired sequence is attached in a subsequent process.

In S140, pixel data of the signal generated from the solid support given by the sequencing in S120 and the measured location data in S130 are mapped. An NGS device provides a signal generated in sequencing along with pixel data of a detector.

The NGS device may provide location data according to a pixel of the signal during the analysis of the DNA. However, a well structure of a substrate of the sequencing device accommodating a microbead (solid support) may not be perfectly regular, a location at which a signal is generated may not be fixed in one microbead, and the imaging system itself may be distorted. Due to the causes described above, there is an error between the pixel data and the physical location data of the microbead, and thus it is almost impossible to trace an exact location of the microbead in an entire region of the substrate.

Accordingly, the measured location data obtained in S130 is precisely mapped with the pixel data obtained in S120 to trace the exact location of the solid support.

For mapping, determination of a reference point by forming a special pattern in a certain region of the sequencing substrate may be included. Here, forming of the special pattern may be performed by extracting the solid supports located in a specific region. Preferably, a Sequence of the oligonucleotide immobilized on the solid supports extracted to set the reference point may be identified. The reference point may be determined by identifying bead data on the pixel data provided from the sequence data previously obtained and matching an actual bead location identified thereby with the pixel data.

According to an exemplary embodiment, for mapping, an algorithm minimizing the error between the pixel data and the measured location data may be used.

To minimize a unique error in the sequencing system, in the specification, a local match expansion algorithm is suggested. Put simply, subdomains having a range in which distortion can be minimized are selected from the entire domain in which irregular distortion occurs. Subsequently, the algorithm is configured to minimize errors due to distortion by defining a function capable of minimizing local matching of a pixel location with a location value of a well from a certain initial subdomain, and finding a local matching function from the certain initial subdomain to the nearest subdomain. According to the algorithm, it is possible to trace an exact location.

According to an exemplary embodiment, the algorithm may include the following method. A set of first subdomains selected as a part of the entire domain including the pixel data, and a set of second subdomains including the measured location data matching the set of the first subdomains, are defined. Due to irregular distortion, it is hard to match all of the pixel data and the measured location data with one linear function. For this reason, the entire domain is divided into subdomains capable of being defined by a local transform function. A set of optimum transform functions with respect to the entire domain is found through local matching for solving optimum transform functions between elements of the first subdomain and elements of the second subdomain.

According to an exemplary embodiment, the first subdomains are composed of single subdomains selected to include a statistically analyzable number of elements. Here, the single subdomain maintains linearity in a level that distortion of the elements is allowable. The entire domain is irregularly and non-linearly distorted because of several reasons on the system. When the entire domain is divided into the local subdomains, non-linear distortion possibly approach approximate to linear distortion.

According to an exemplary embodiment, the optimum transform function may be derived from an optimum result of feedback calculation that applies an optimum transform function corresponding to a certain first subdomain to an initial value for an optimum transform function in another first subdomain nearest to the certain first subdomain.

In S150, the solid support having a desired DNA sequence is extracted from the sequencing substrate using the mapping result. For the extraction, a pulsed laser beam may be incident on the sequencing substrate on which the solid support is placed.

A pulsed laser beam condensed through an objective lens is controlled to be focused at an approximate location in an imaging plane of the sequencing substrate, so that its energy is condensed to the location in a micrometer scale.

Specifically, for the extraction, pulsed laser ablation or radiation pressure ejection may be used. As an example of a technique of transferring a micro structure using a pulsed laser, laser direct writing (LDW) or laser capture microdissection (LCM) is used. LDW is a technique of ablating a substrate using energy of a condensed pulsed laser and moving a desired material to another substrate using a pressure generated during the ablation. Meanwhile, LCM is a technique of moving a thinly peeled cell to another substrate using radiation pressure of a pulsed laser for post-treatment. According to such a mechanism of the pulsed laser, a microbead having a specific DNA may be extracted from the substrate of the NGS device. It is a non-contact method using an optical device, and does not result in cross-contamination. Therefore, mass-production of high-purity oligonucleotides is possible and optical observation is easily performed. Consequently, these methods can compensate for disadvantages of the pick-and-place method, they have a short extraction time, and thus they may be the most practical and positive alternative.

Through the extraction, the solid support is transferred from the sequencing substrate to a separate matching substrate. The matching substrate may be a substrate for amplifying DNA. For example, the matching substrate may be a PCR plate or PCR tube rack.

The matching substrate may include a plurality of wells to accommodate the solid supports. The wells of the matching substrate may match wells of a sequencing substrate such as a 454 plate.

In S160, an oligonucleotide on the extracted solid support may be amplified to replicate on a large scale. To amplify the oligonucleotide by an amount required for an experiment, PCR may be performed.

According to the above-described method, high-purity oligonucleotides having various kinds of DNA may be rapidly prepared at a low cost.

According to an exemplary embodiment of the present disclosure, a solid support extraction system for mass-producing the high-purity nucleotides is provided. The system includes a first stage equipped with a sequencing substrate accommodating a solid support to which an oligonucleotide having a specific DNA is bound; a first imaging device for observing the sequencing substrate to extract the solid support; a second stage equipped with a matching substrate disposed opposite to the sequencing substrate; an extracting device for separating the solid support from the sequencing substrate and transferring it to the matching substrate; and a control device locating a specific region of the sequencing substrate matching the extracting device to separate the solid support. In this case, the locating operation is executed using a mapping result between measured location data of the solid support obtained by the first imaging device and pixel data of a signal generated from the solid support.

According to an exemplary embodiment, the extracting device may include a pulsed laser source and a condenser.

According to an exemplary embodiment, the system may further include a second imaging device to observe the matching substrate to collect the solid support.

Figure 2:
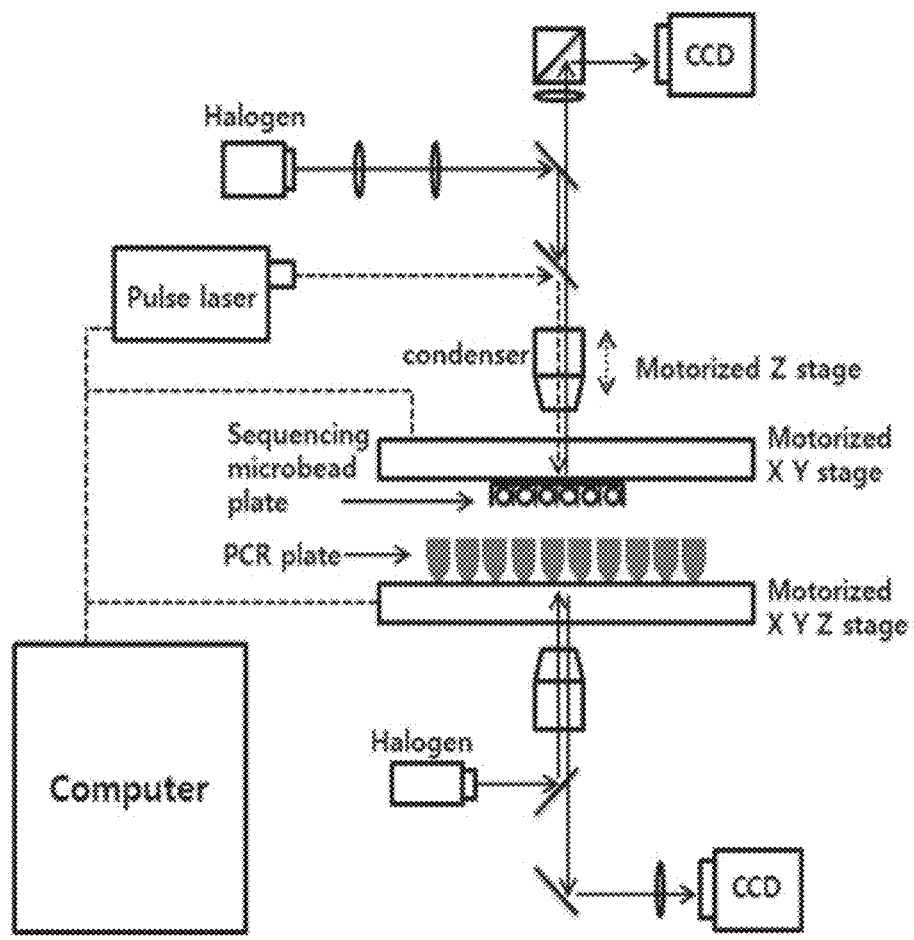
FIG. 2 is a diagram of a solid support extraction system according to an exemplary embodiment of the present disclosure.

FIG. 2 is a diagram of a solid support extraction system according to an exemplary embodiment. Referring to FIG. 2, the entire system is mainly divided into an upper system and a lower system. The upper system is composed of an upper stage (motorized XY stage) and a pulsed laser, which are controlled by a computer, having an NGS substrate attached below, and an imaging device.

The upper system, having infinite optical system, may include a pulsed laser spot and an imaging plane, which are set almost sideways, to observe a location of a well in a 454 plate (sequencing plate), and to control and determine a spot location of the pulsed laser by vertical movement of an objective lens. When the location of the pulsed laser spot is input to an algorithm, the pixel data is compared with an actual physical location of a well, and then a physical location of a corresponding DNA sequence is extracted. When location data of a microbead having a desired specific DNA is provided to the upper stage equipped with the sequencing substrate, the pulsed laser spot moves to a corresponding location. Simultaneously, the lower stage and a PCR plate, which is a matching substrate, installed at the lower stage, may be located close to the sequencing substrate in a Z direction, and thus a well of the PCR plate may receive the sequentially extracted microbead below.

A pulsed laser beam condensed through a condenser is incident on the sequencing substrate including a microbead to push the corresponding microbead to the underlying PCR plate (matching substrate) by expansion pressure due to ablation or radiation pressure. The lower system is composed of a lower stage (motorized XYZ stage) having a PCR tube rack or PCR plate as a matching substrate of an upper part of the lower system, to move along a Z axis, and an imaging system disposed under the lower stage. The underlying imaging system is used to optically identify a microbead when the microbead is collected using a flat bottom PCR plate or another matching substrate capable of transmission imaging, or to determine a physical reference location of a well. In addition, the lower imaging system may be used to provide transmitted light to an upper imaging system, since the presence or absence of the microbead may be identified only with the transmitted light when the microbead is observed by the upper imaging system, due to characteristics of the 454 plate.

Figure 3:
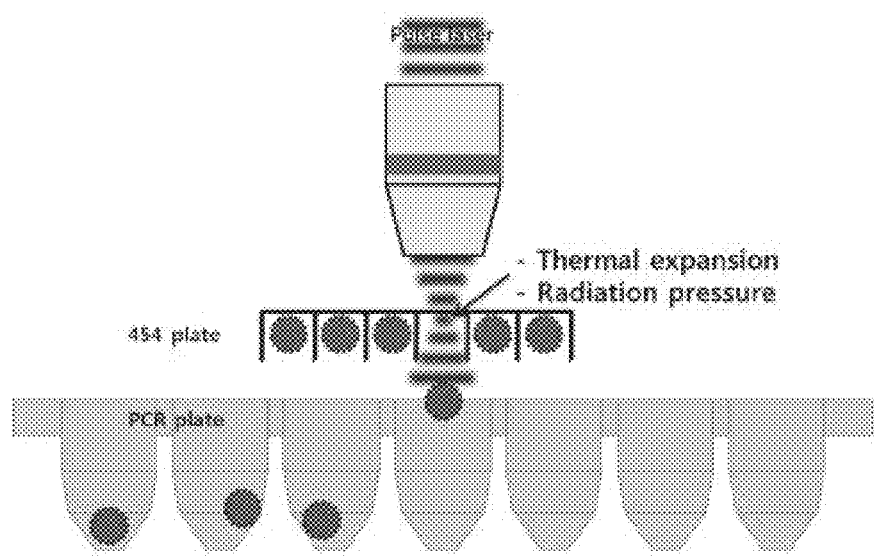
FIG. 3 is a schematic diagram illustrating a principle of extracting a solid support.

FIG. 3 is a schematic diagram illustrating a principle of extracting a solid support. Referring to FIG. 3, a pulsed laser beam condensed through an objective lens allows expansion pressure due to ablation or radiation pressure to act on a corresponding solid support at a focus, thereby separating and releasing the solid support from the 454 plate to PCR plate.

There are various types of methods of extracting the solid support using the pulsed laser. The extraction method includes a method of allowing the pulsed laser beam to be incident on a sequencing substrate on which a solid support is placed or a separate substrate including the solid support derived from the sequencing substrate.

Figure 4:
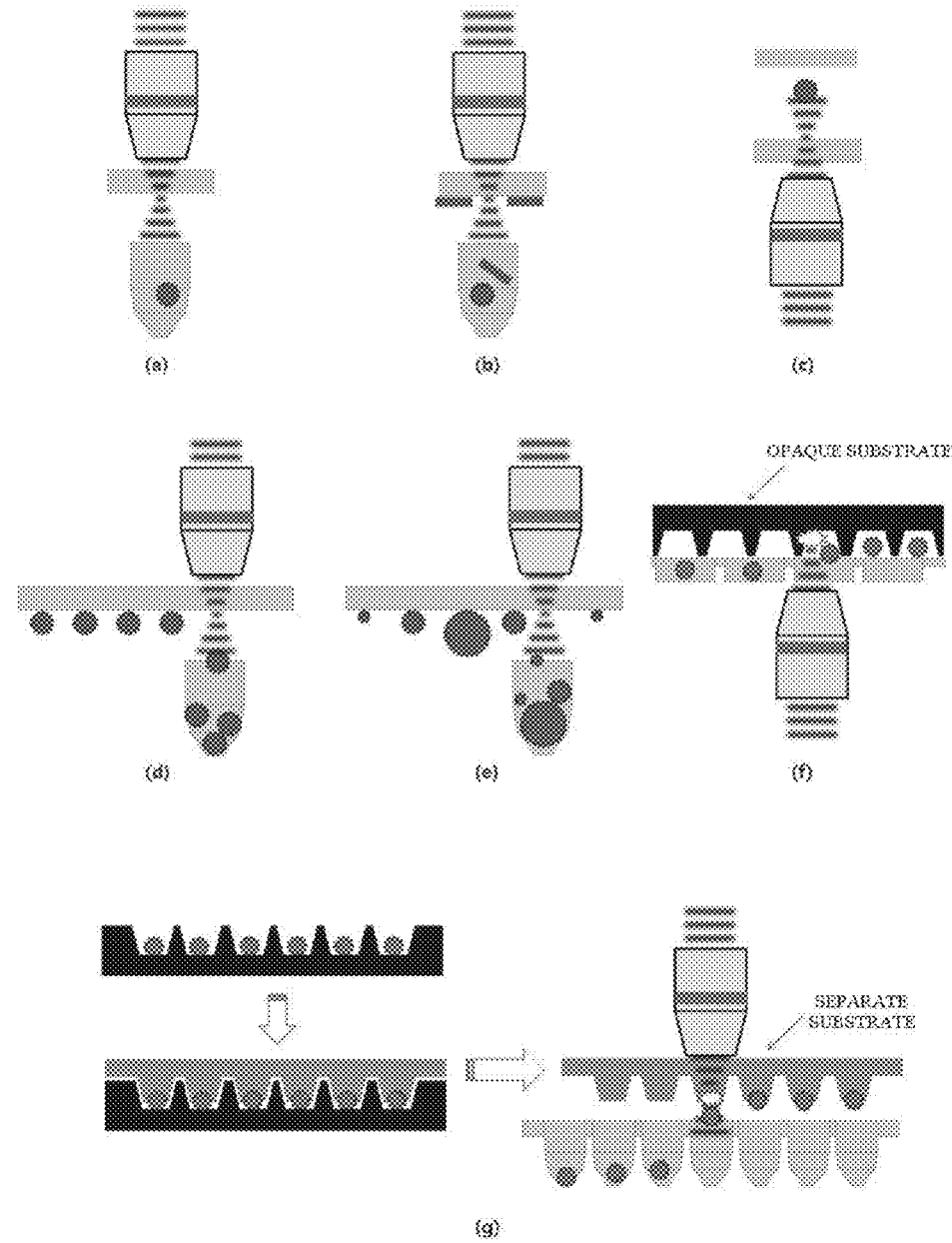
FIG. 4 illustrates various examples of extracting a solid support using the solid support extraction system.

FIG. 4 shows various examples of extracting a solid support using a solid support extraction system. Referring to FIG. 4, a) is a conventional method of applying light to a backside of a microbead attached to a bottom of a substrate to push the microbead downward, b) is a method, similar to a), of applying condensed light to a sacrificial region formed between a microbead and a substrate to minimize damage to the microbead, c) is the same as a) except that the light is applied from a bottom of a substrate and a new substrate on which a microbead moves is adhesive, thereby fixing a location of the bead not to be detached by gravity, and d) is a method of collecting at least one bead having a different kind of DNA. According to d), labor required for initial assembly of DNA may be reduced. Here, e) is a method of collecting at least one of various kinds of beads in one tube, and f) is a method of condensing a pulsed laser on a surface of the substrate having a well and extracting a solid support to a matching substrate capable of transmission imaging, which is present at a side from which light is incident, when backside incidence of light is impossible due to an optically opaque sequencing substrate including a solid support. A condensing point of the pulsed laser is intentionally off from a center of a well or microbead to increase an efficiency of separating a microbead. In g), a transparent substrate is separately introduced to facilitate extraction when a sequencing substrate is optically opaque. The transparent substrate may be composed of an adhesive or curable material to transfer a solid support from the sequencing substrate. Due to the transparent substrate, the solid support may be separated from the opaque substrate while maintaining location data, and extracted by the methods of a) to e).

Besides these examples, there may be various other methods of extracting a solid support using a pulsed laser.

Hereinafter, as an aspect of an exemplary embodiment of the present disclosure, a mapping process, which is required for extracting a desired solid support, will be described in detail.

To extract a desired bead from a sequencing substrate such as a 454 plate, it is necessary to match a pixel data set of a bead given as a result of sequencing with a location data set of a bead given by scanning the sequencing chip on the system of the present disclosure. The former data set refers to a set $A=\{X_1, X_2, \ldots, X_{Nseq}\}$, the latter data set refers to a set $B=\{X'_1, X'_2, \ldots, X'_{Nscan}\}$, and elements of A and B denote locations of beads in a two-dimensional coordinate space, respectively. $N_{seq}$ and $N_{scan}$ may not be the same as each other, because even a well having a bead may not be sequenced, and even a sequenced well may not be recognized during scanning. The elements of A and B denote locations of beads in different coordinate spaces, respectively, and a process of matching elements of A and B expressing locations of the same beads is referred to as "mapping."

Figure 5:
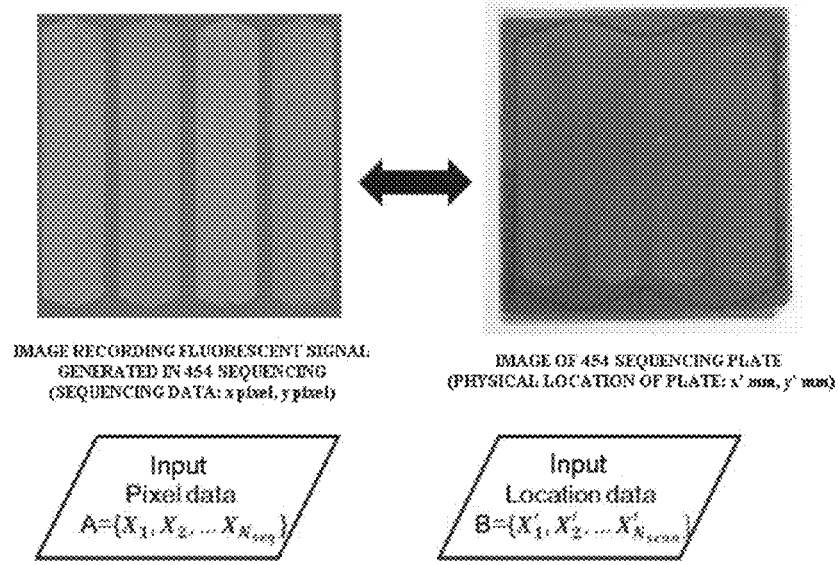
FIG. 5 illustrates a mapping process between pixel data in which a sequencing result is recorded and a physical location of a molecular clone.

FIG. 5 illustrates a mapping process between pixel data in which a sequencing result is recorded and a physical location of a molecular clone.

<Descriptions of Mapping Step>

1. Extraction of Input Location Data

1) A sequencing substrate having a clonal library of oligonucleotides on a solid support is provided.

2) Pixel data of the solid support having a specific DNA sequence is obtained by sequencing the clonal library. This data represents input pixel data, A, as described above.

Figure 6:
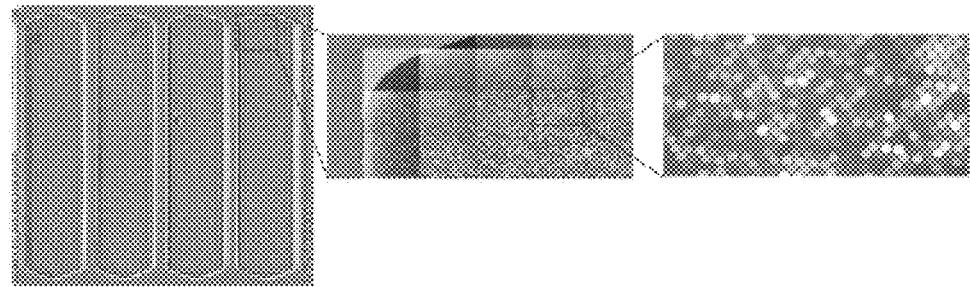
FIG. 6 is an image obtained by scanning a sequencing substrate.

3) Measured location data of the solid support on the sequencing substrate is obtained. This step includes sub-steps as follows:

① Scanning of Substrate: The provided sequencing substrate is scanned step by step using a very precisely-operated motorized stage to measure an actual location of a microwell. This is a preparation for obtaining data of an actual relative location from a certain reference point. FIG. 6 is an image obtained by scanning the sequencing substrate.

Figure 7:
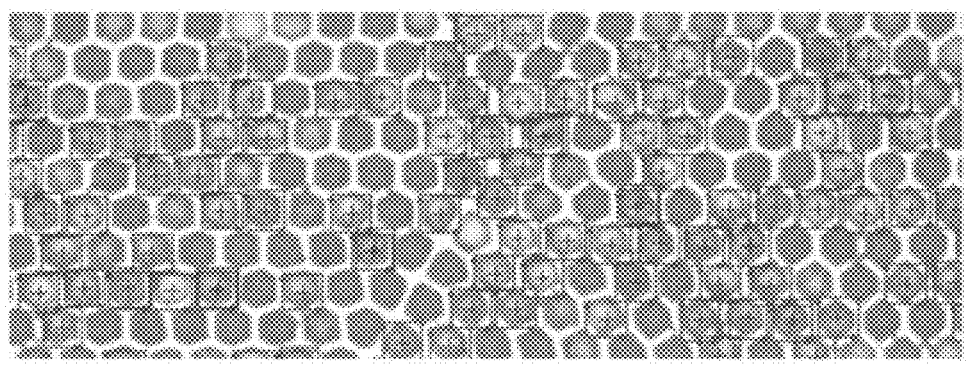
FIG. 7 illustrates a location of a center of a microbead (or microwell) by processing a scanned image.

② Recognition of Microbead (or microwell): A center of a microbead (or microwell) is located by processing a divided image obtained by scanning using a pattern recognition algorithm. FIG. 7 illustrates a center of the microbead (or microwell) located by processing the scanned image.

③ Extraction of Coordinate: The location of the center of the microbead (or microwell) found by the pattern recognition is extracted as a coordinate with respect to the entire substrate. Here, a certain reference point is determined, and an actual relative location coordinate is estimated from the reference point. The location coordinate becomes the second input location data, B, described above.

2. Determination of Reference Point

A reference point may be determined by intentionally extracting a bead in a specific region from a sequencing substrate to form a special pattern, sequencing a DNA of the bead again, and matching an actual bead location with pixel data.

① A bead in a specific region is extracted based on a desired pattern using various available techniques including extraction using a pulsed laser.

② The extracted bead is amplified by PCR and purified, and then DNA sequence data of the bead is obtained again using Sanger sequencing.

③ A reference point is determined by confirming bead data on pixel data provided from the DNA sequencing data previously obtained and matching an actual location of the bead with the pixel data.

Figure 8:
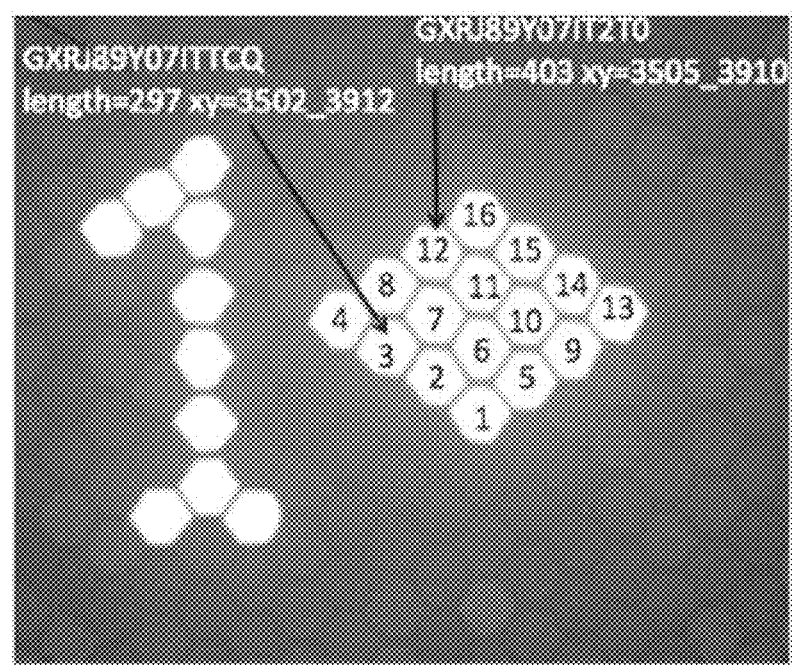
FIG. 8 illustrates a result of matching pixel data with a coordinate indicating a physical location of a molecular clone on a substrate.
Figure 9A:
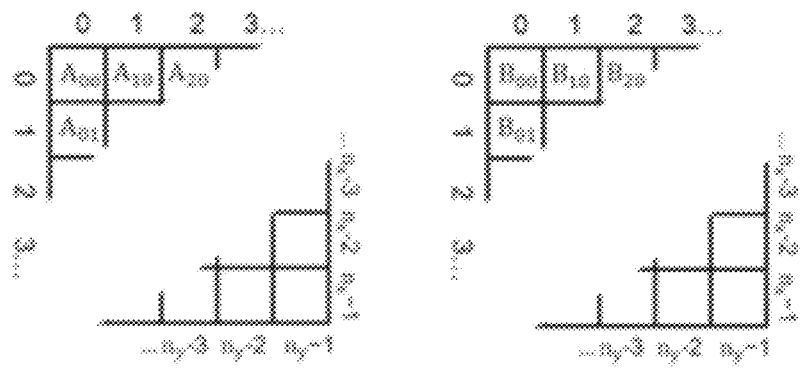
FIGS. 9 (*a*) to (*d*) illustrate an algorithm for matching pixel data with location data.
Figure 9B:
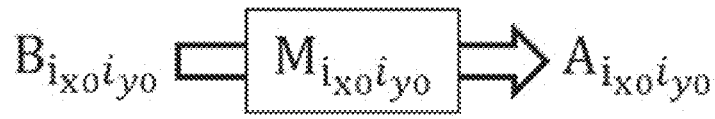
Figure 9C:
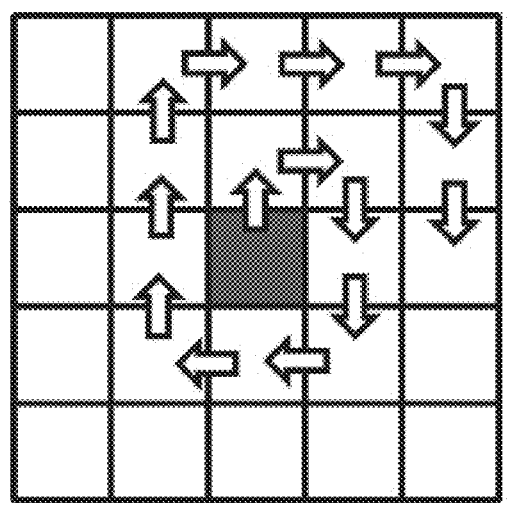
Figure 9D:
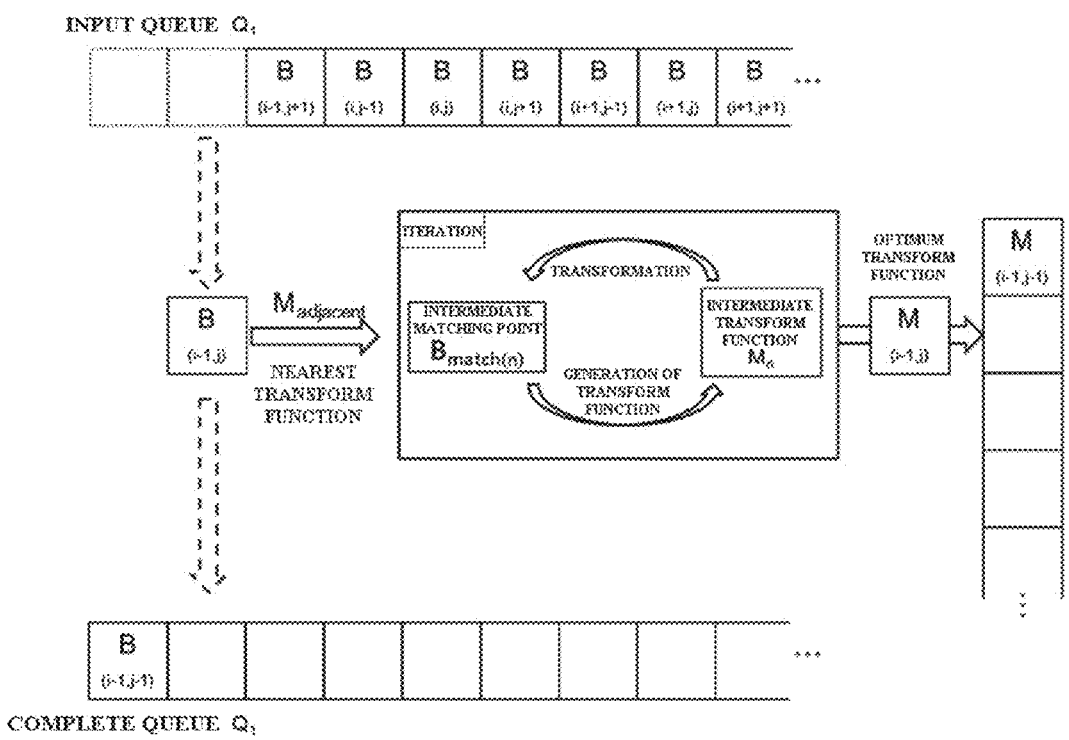

FIG. 8 illustrates a matching result between matching pixel data and coordinates indicating a physical location of a bead on a sequencing substrate. Referring to FIG. 8, a bright part is a special pattern generated by extracting the bead. Numbers in the bright part denote an order of the extracted beads. Data indicated by arrows are next generation sequencing results for a bead at each location, which include an ID of the corresponding DNA sequence, a length of the DNA, and pixel data at the corresponding matched location.

3. Matching of Pixel Data (A) with Location Data (B)

This is a key step of this technique. Put simply, the step is as follows: A and B are separated into small subdomains, and a transform function is found from a region having the reference point previously determined. A method of obtaining a transform function with respect to one set of subdomains (a subdomain of A and a subdomain of B matching therewith) is repeated calculation such as a feedback method. When matching points are obtained using the first-found transform function, the number of points matching precisely is very small. A matching function on a two-dimensional plane mathematically needs only three points. When an initial transform function is matched with more than three points, a transform function matching the maximum number of points is selected by iteration or iterative calculation including creating another transform function based on the matching points, executing matching again using the created function to create a match function with increased points, among the match functions created thereby, selecting a function having the greatest number of matching points, and obtaining matching points again using the selected function to create a match function. The selected transform function is determined as a transform function for a set of subdomains. Afterward, to find a transform function of another set of subdomains which are nearest to the subdomain, a transform function which is the most suitable for next subdomains is found through iteration or iterative calculation with the transform function previously calculated as an initial transform function. This is done to find a transform function progressing in a specific direction in a space, and expand a matched region. As a result, there are as many transform functions as sets of subdomains.

FIGS. 9 $a$) to $d$) illustrate an algorithm for matching pixel data with location data.

1) Creation of Subdomain: The entire domain is divided into spatially small subdomains. This is because errors that can occur in a system are minimized by limiting a subdomain.

To express elements of A and B in rectangular coordinates, ranges of x and y in which data are distributed are equally divided into $n_x$ and $n_y$, indexes of each section are denoted as $i_x$=0, 1, 2, ..., $n_x$−1 and $i_y$=0, 1, 2, ..., $n_y$−1. In addition, $A_{ij}$ is defined as a set of elements included in $i_x$=i, $i_y$=j, among the elements of A. Likewise, $B_{ij}$ is defined as a set of elements included in $i_x$=i, $i_y$=j, among the elements of B (see FIG. 9$a$)).

2) an Initial Domain is Set, and a Transform Function in the Domain is Defined.

The initial domain is defined as a subdomain in which a location of a pixel or an actual location of a bead obtained by scanning a structure is found to match in the determination of the reference point. That is, a subdomain of A including a pixel as a reference point and a subdomain of B including a bead as a reference point are the initial domains, and an initial transform function is defined with matching points in the two regions. Since a signal from the bead is not always generated from a center of the bead in determining matching points, the matching points do not completely overlap. Therefore, when one point of A and one point of B are within a specific range of distance, it may be assumed that these points match. Like the initial transform function, a function matching the maximum number of points through iteration or iterative calculation is determined as a final transform function.

The initial domain may be a region expressed as $i_x$=$i_{x0}$, $i_y$=$i_{y0}$, and determined by certain values. After determining the initial domain, elements of $B_{i_{x0}i_{y0}}$ are matched with element of $A_{i_{x0}i_{y0}}$ through morphism $M_{i_{x0}i_{y0}}$ at the initial domain. At this time, $M_{i_{x0}i_{y0}}$ is determined to have the maximum number of "matches" between element of $A_{i_{x0}i_{y0}}$ and element of $B_{i_{x0}i_{y0}}$ as showed in FIG. 9$b$. Here, the morphism M refers to a function mapping a coordinate space having an element of B to a coordinate space having an element of A. Here, the "match" refers to a pair $(X_p, Xq')$ having a distance between the element of A and the element of B of a specific threshold or less ($p \in \{1, 2, \ldots, N_{seq}\}$, $q \in \{1, 2, \ldots, N_{scan}\}$).

3) Generation of Queue: A queue is generated by putting a set of subdomains (sets of indexes) for which transform functions have yet to be found to $Q_1$, before a final transform function is found from the set of subdomains, and putting a set of subdomains (set of indexes) for which transform functions have been found to $Q_2$ after a final transform function is found from the set of subdomains, thereby preventing repeated calculation and expanding matching regions.

The queue refers to a queue of a data structure, and queues $Q_1$ and $Q_2$ are defined. Mapping of indexes input to the queue $Q_1$ is sequentially executed, and the complete mapped index is input to an element of queue $Q_2$.

A pair of indexes in the initial domain is input to an element of a queue.

An index in the initial domain is input as an initial value of an input queue to calculate a transform function, and another transform function of a subdomain having the nearest index to the index in the initial domain (also the most close thereto spatially) is found by the same method as described above. Here, calculation with respect to a set of subdomains is executed by calculating an index only in an input queue, not a complete queue.

4) Addition to Queue of Index Adjacent to Index Corresponding to First Element of Queue When an index is adjacent to another index, it means that elements of indexes have a difference of 1. In other words, indexes adjacent to index (i, j) are (i−1, j−1), (i−1, j), (i−1, j+1), (i, j−1), (i, j), (i, j+1), (i+1, j−1), (i+1, j), and (i+1, j+1). Among the nine adjacent indexes, an index not included in Q2 is inserted into Q1. An order of insertion of the adjacent indexes into Q1 may be randomly determined.

As shown in FIG. 9 $c$), a final transform function is found through iteration or iterative calculation from the initial domain, and then subsequent calculation is executed in a random direction. The presence of a queue is to prevent repeated calculation and specify a direction of calculation, so that calculation does not backtrack.

5) Searching for Morphism Nearest to Index Corresponding to First Element of Q1 Among Indexes of Morphism (Transform Function)

To find a set of subdomains present in a certain direction from the initial domain, an initial value for iteration or iterative calculation is needed. A final transform function of a set of subdomains located spatially nearest to the initial domain is the most suitable for an initial transform function of a transform function of a new set of subdomains. In calculating to find a transform function in a specific subdomain in such a manner, an initial transform function for iteration or iterative calculation uses a transform function of the spatially nearest region. An index of morphism $M_{i_m j_m}$ is $(i_m, j_m)$, and a distance from index (i, j) is $\sqrt{(i_m-i)^2+(j_m-j)^2}$.

6) Definition of Final Transform Function through Iteration or Iterative Calculation: Matching points of A and B are found using the initial transform function found in step 5). These matching points are not optimal solutions, and thus a final transform function matching the maximum number of points is found through iteration or iterative calculation. The purpose of the iteration or iterative calculation is to find the first matching point using a final transform function of a spatially nearest set of subdomains, which is defined as an initial transform function of a current set of subdomains. If there is no error due to two-dimensional planar matching, mathematically, a matching function may be perfectly found with at least three points. Therefore, a second transform function is also found with matching points using the initial transform function, and then A and B are matched again using the second transform function, thereby increasing the probability of obtaining more and more precise matches than the matching points found from the initial transform function. The above-mentioned process is repeated enough times to define a transform function having the maximum number of matching points as a final transform function of a corresponding subdomain, and to use the final transform function as an initial transform function of a next subdomain.

In other words, the process is as follows: the morphism obtained in step 5) matched with the region corresponding to the first element of $Q_1$, thereby finding matches. A new morphism is found using the matches. Then, a morphism corresponding to a corresponding region is matched again with the previously-found morphism, and matches are found again. Such a process is repeated a predetermined number of times, and a morphism used when the largest number of matches are found is determined as the morphism of the region. In other words, when an index of the region is $(i_x, j_y)$, $M_{i_m j_m}$ is defined as a morphism used when the largest number of matches are found. In addition, matches of A and B elements found using the morphism are stored.

7) Determination of Matching Direction

A process of determining a matching direction will be described with reference to FIG. 9 d).

A calculating direction is set by determining an input queue and a complete queue by the same method as described above, and an end of algorithm is defined. The first element of $Q_1$ is removed and then inserted into $Q_2$.

The input queue has a sequence of indexes of a total of nine subdomains including an initial domain. Addition of an index of a subdomain to be sequentially calculated is executed as follows. After a second round of calculation, adjacent subdomains (eight regions) are added. The subdomains except (an index of) a subdomain included in the complete queue after calculation and a subdomain already included in the input queue are added to the input queue. By doing this, repeated calculation can be prevented, and matching can progress in a specific direction in a space.

If there is no (index of) subdomain remaining in the input queue, calculation is terminated, and coordinates of the matching points are stored to be provided as data enabling movement on an actual motorized stage.

<Confirmation of Results>

1. Errors and mistakes derived from a system were minimized by finding optimum solutions with respect to transform functions for local subdomains. FIG. 10 illustrates matching results between two groups of data represented on an entire region of a sequencing substrate.

2. FIG. 11 illustrates composition of pixel data and location data obtained by mapping to confirm the results.

Figures 12, 13:
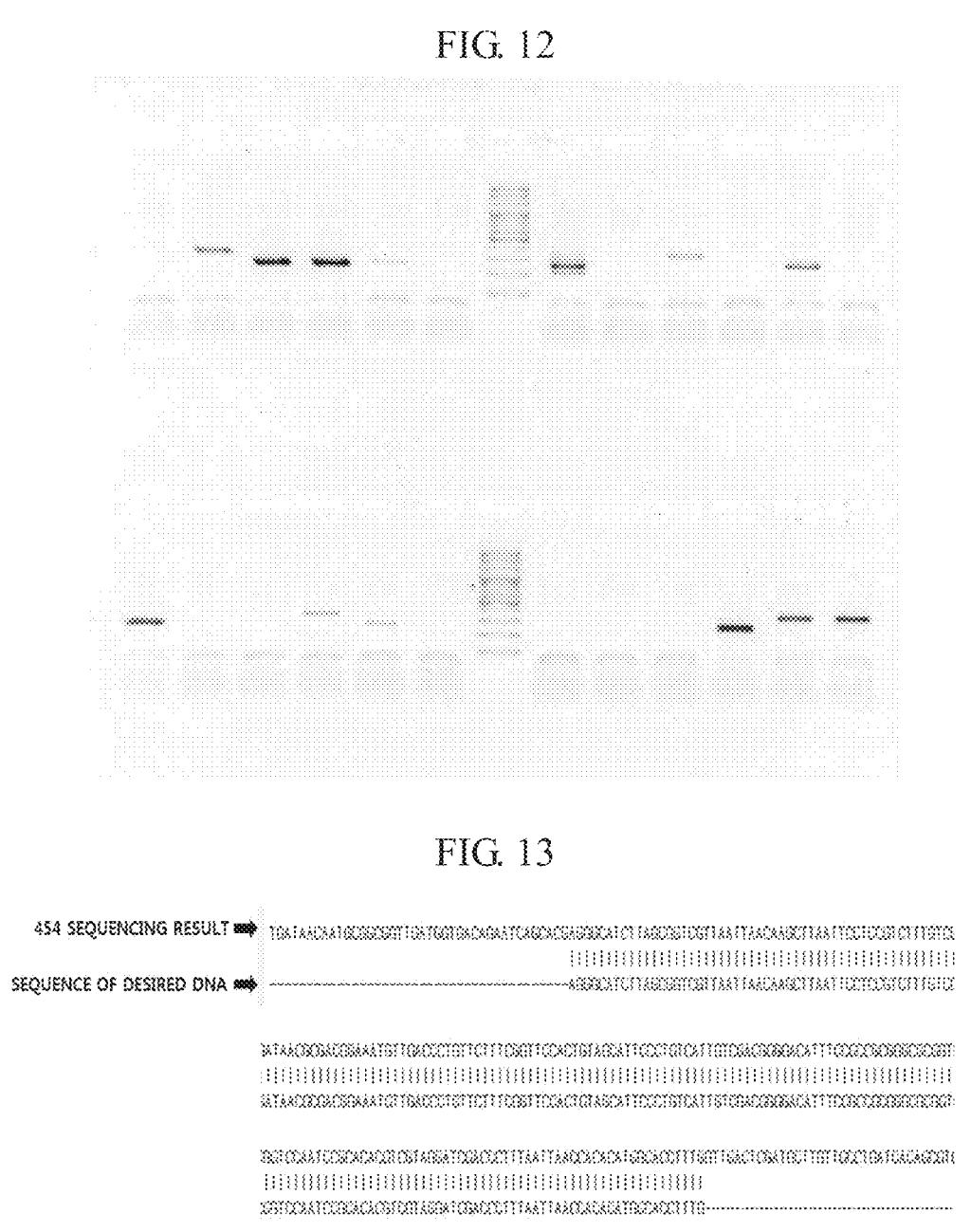

3. A bead was extracted based on the obtained location data using a laser and amplified by PCR, and then bands were identified by electrophoresis. FIG. 12 illustrates electrophoresis results for the bead extracted by a bead extraction system using a laser after amplification by PCR.

4. Verification of the technique suggested as a process of separating and purifying a band obtained by the electrophoresis, and confirming whether the band is or is not identical to a target DNA through Sanger sequencing is finished. FIG. 13 illustrates alignment of a DNA sequence included in the extracted bead by mapping to the target DNA sequence. Referring to FIG. 13, the DNA sequence of the extracted bead matches the target DNA sequence.

The NGS analysis analyzes and provides a large quantity of DNA sequence data within a short time. At the same time, the DNA synthesis using a microarray can synthesize several hundreds of independent DNA libraries at a time. According to the present disclosure described above, a location of a desired microbead can be precisely traced from a sequencing substrate that has been through sequencing by mapping using an algorithm. In addition, DNA can be extracted and amplified by a high-speed and non-contact method based on a pulsed laser, thereby making a breakthrough in genetic engineering and synthetic biology, mostly in biology.

Oligonucleotides prepared using the method of mass-producing high-purity oligonucleotides described above may be applied in various fields. When such high-purity nucleotides are applied to analysis of single nucleotide polymorphism, the analysis can be more precisely executed by reducing signal noise than when using oligonucleotides having errors prepared by the conventional method.

According to the technique described above, high-purity oligonucleotides having various kinds of DNA can be prepared, which are used more effectively to search a ribonucleotide. Solid supports on which respective deoxynucleotides are immobilized are put into different reactors, and deoxyribonucleotides are transferred from an external environment, thereby preparing a ribonucleotide. The prepared ribonucleotide can be applied to search for ribonucleotides such as miRNA, siRNA, and RNAi.

Using the error-less high-purity oligonucleotides described above, a long DNA can be synthesized with a drastically increased yield. Generally, to prepare a deoxynucleotide having a long DNA sequence, oligonucleotides having a short DNA sequence are bound to make a long DNA (100 to 100,000,000 bp). An oligonucleotide having a short DNA sequence prepared by the conventional method has a high error rate. Since the error rate increases exponentially when oligonucleotides are bound to make a long DNA, the error rate of a final product is very high.

When external expression of protein is induced using high-purity oligonucleotides having various kinds of DNA sequences disclosed herein, it may be applied to production of a codon-optimized gene, antibody optimization, and the search for cancer genes. In addition, when external translation is induced using an oligonucleotide produced by the technique disclosed herein, various kinds of proteins may be easily expressed.

While the disclosure has been shown and described with reference to certain exemplary embodiments thereof, it will be understood by those skilled in the art that various changes in form and details may be made therein without departing from the scope of the disclosure as defined by the appended claims.

What is claimed is:

1. A method of producing high-purity oligonucleotides, comprising the steps of:
providing a sequencing substrate having a clonal library of oligonucleotides on solid supports, wherein the solid supports are disposed in a predetermined section of the sequencing substrate;
sequencing the clonal library and generating optical or electromagnetic signals of the clonal library;
obtaining pixel data of a signal generated from each of the solid supports having a selected DNA sequence during the sequencing step;
obtaining measured location data of the solid support on the substrate by scanning the substrate with an imaging device;
mapping the pixel data with the measured location data of the solid supports,
wherein an algorithm is used in the step of mapping for tracing an exact location of each solid support;
performing the algorithm comprising:
dividing an entire domain of the substrate into a plurality of spatially small subdomains,
selecting one subdomain (i, j) among the plurality of subdomains, the one subdomain defines where a location of the pixel data and the measured location data is matched,
defining a transform function of the one subdomain by applying the matched pixel data and the measured location data,
defining an input queue having adjacent subdomains which are adjacent to the one subdomain (i, j),
wherein the adjacent subdomains are (i−1, j−1), (i−1, j), (i−1, j+1), (i, j−1), (i, j+1), (i+1, j−1), (i+1, j), and (i+1, j+1),
defining a next transform function by applying any one of the adjacent subdomains to the transform function which is previously defined,
wherein the applied adjacent subdomain is added into a complete queue so that the applied adjacent subdomain is not repeatedly applied, wherein the complete queue includes the adjacent subdomains different from the input queue,
wherein an order of applying the adjacent subdomain defines a matching direction, and
determining transform functions corresponding to each subdomain of the entire domain by expanding the matching direction via repeating the step of defining the input queue and the stet of defining the next transform function,
wherein at least three mapped data are provided to trace the exact location of each solid support;
extracting the solid supports having the selected DNA sequence from the sequencing substrate by a pulsed laser beam, wherein each solid support is extracted based on the algorithm; and
amplifying an oligonucleotide on the extracted solid supports to produce a plurality of the high-purity oligonucleotides by replication.

2. The method of claim 1, further comprising, determining a reference point by extracting the solid support located in a region of the sequencing substrate.

3. The method of claim 1, wherein in the step of extracting, the solid supports are executed by pulsed laser ablation or radiation pressure ejection.

4. The method of claim 1, wherein, through the step of extracting the solid supports, the solid supports move from the sequencing substrate to a receiver.

5. The method of claim 4, wherein the receiver is configured to amplify DNA.

6. The method of claim 4, wherein the receiver includes a plurality of wells.

7. The method of claim 1, wherein the extracting step is executed by placing a sacrificial region between the sequencing substrate and the solid support and moving the solid supports to a receiver.

8. The method of claim 1, wherein the extracting step is executed by moving the solid supports to an adhesive receiver.

9. The method of claim 1, wherein the extracting step is executed by moving the solid supports to a receiver from the sequencing substrate, and by moving the solid supports to one of a plurality of wells.

10. A method of producing high-purity oligonucleotides, comprising the steps of:
    providing a first sequencing substrate having a clonal library of oligonucleotides on solid supports, wherein the solid supports are disposed in a predetermined section of the first sequencing substrate;
    sequencing the clonal library and generating optical or electromagnetic signals of the clonal library;
    obtaining pixel data of a signal generated from each of the solid supports having a selected DNA sequence during the sequencing step;
    obtaining measured location data of the solid support on the first substrate by scanning the first substrate with an imaging device;
    mapping the pixel data with the measured location data of the solid supports,
    wherein an algorithm is used in the step of mapping for tracing an exact location of each solid support;
    performing the algorithm comprising:
    dividing an entire domain of the substrate into a plurality of spatially small subdomains,
    selecting one subdomain (i, j) among the plurality of subdomains, the one subdomain defines where a location of the pixel data and the measured location data is matched,
    defining a transform function of the one subdomain by applying the matched pixel data and the measured location data,
    defining an input queue having adjacent subdomains which are adjacent to the one subdomain (i, j), wherein the adjacent subdomains are (i−1, j−1), (i−1, j), (i−1, j+1), (i, j−1), (i, j+1), (i+1, j−1), (i+1, j), and (i+1, j+1),
    defining a next transform function by applying any one of the adjacent subdomains to the transform function which is previously defined,
    wherein the applied adjacent subdomain is added into a complete queue so that the applied adjacent subdomain is not repeatedly applied, wherein the complete queue includes the adjacent subdomains different from the input queue,
    wherein an order of applying the adjacent subdomain defines a matching direction, and
    determining transform functions corresponding to each subdomain of the entire domain by expanding the matching direction,
    wherein at least three mapped data are provided to trace the exact location of each solid support;
    extracting the solid supports having the selected DNA sequence from the first sequencing substrate by a pulsed laser beam, each solid support be extracted based on the algorithm, wherein the step of extracting the solid support comprises,
    transferring the solid supports from the first sequencing substrate to a second substrate, and
    applying the pulsed laser beam to the second substrate having the solid supports which are transferred from the first sequencing substrate; and
    amplifying an oligonucleotide on the extracted solid supports to produce a plurality of the high-purity oligonucleotides by replication.

11. The method of claim 10, wherein the second substrate has adhesion and curability.

* * * * *

SEQUENCE LISTING

<160> NUMBER OF SEQ ID NOS: 2

<210> SEQ ID NO 1
<211> LENGTH: 276
<212> TYPE: DNA
<213> ORGANISM: Artificial Sequence
<220> FEATURE:
<223> OTHER INFORMATION: Synthetic Oligonucleotide

<400> SEQUENCE: 1
tgataacaat gcggcggttg atggtgacag aatcagcacg agggcatctt agcggtcgtt      60
aattaacaag cttaattcct ccgtctttgt cgataacgcg acggaaatgt tgaccctgtt     120
ctttcggttc cactgtagca ttccctgtca ttgtcgacgg ggacatttcc gccgcgggcg     180
cggtggtcca atccgcacac gtcgtaggat cgacccttta attaaccaca catggcacct     240
ttggttgact cgatgcttgt tgcctgatca cagcgt                               276

<210> SEQ ID NO 2
<211> LENGTH: 203
<212> TYPE: DNA
<213> ORGANISM: Artificial Sequence
<220> FEATURE:
<223> OTHER INFORMATION: Synthetic Oligonucleotide

<400> SEQUENCE: 2
agggcatctt agcggtcgtt aattaacaag cttaattcct ccgtctttgt cgataacgcg      60
acggaaatgt tgaccctgtt ctttcggttc cactgtagca ttccctgtca ttgtcgacgg     120
ggacatttcc gccgcgggcg cggtggtcca atccgcacac gtcgtaggat cgacccttta     180
attaaccaca catggcacct ttg                                             203